(12) United States Patent
O'Lenick, Jr.

(10) Patent No.: US 6,346,595 B1
(45) Date of Patent: Feb. 12, 2002

(54) AROMATIC DIMETHICONE COPOLYOL POLYMERS AS SUNSCREEN AGENTS

(75) Inventor: Anthony J. O'Lenick, Jr., Dacula, GA (US)

(73) Assignee: Siltech LLC, Dacula, GA (US)

( * ) Notice: Subject to any disclaimer, the term of this patent is extended or adjusted under 35 U.S.C. 154(b) by 0 days.

(21) Appl. No.: 09/611,553

(22) Filed: Jul. 7, 2000

(51) Int. Cl.$^7$ .......................... C08G 77/04; C08G 77/06
(52) U.S. Cl. ........................... 528/29; 528/25; 528/31; 528/33; 556/445; 556/449; 556/450; 556/453; 556/478; 556/487; 556/489
(58) Field of Search ............................ 528/25, 29, 31, 528/33; 556/445, 449, 450, 453, 478, 487, 489

(56) References Cited

U.S. PATENT DOCUMENTS

| | | | |
|---|---|---|---|
| 5,466,768 A | | 11/1995 | Yang |
| 5,542,960 A | * | 8/1996 | Grabowski .................. 44/320 |
| 5,986,022 A | * | 11/1999 | Austin et al. .................. 526/65 |
| 6,093,222 A | * | 7/2000 | Grabowski et al. ........... 44/320 |
| 6,162,330 A | * | 12/2000 | Northfleet et al. ....... 162/164.4 |

FOREIGN PATENT DOCUMENTS

| | | | |
|---|---|---|---|
| WO | WO 86/05411 | * | 9/1986 |

\* cited by examiner

*Primary Examiner*—Robert Dawson
*Assistant Examiner*—Jeffrey B. Robertson

(57) ABSTRACT

The present invention relates to novel dimethicone copolyol compounds bearing ultra violet absorbing substituents. This invention also relates to compositions of matter, in particular cosmetic compositions, comprising the above novel compounds, which are especially well suited for the photo-protection of the skin and/or the hair against the deleterious effects of UV radiation, in particular solar radiation.

17 Claims, No Drawings

AROMATIC DIMETHICONE COPOLYOL POLYMERS AS SUNSCREEN AGENTS

BACKGROUND OF THE INVENTION

1. Technical Field of the Invention

The present invention relates to novel dimethicone copolyol compounds bearing ultra violet absorbing substituents. This invention also relates to compositions of matter, in particular cosmetic compositions, comprising the above novel compounds, which are especially well suited for the photoprotection of the skin and/or the hair against the deleterious effects of UV radiation, in particular solar radiation.

2. Description of the Prior Art

It is known to this art that light radiation of wavelengths of from 280 nm to 400 nm promotes tanning of the human epidermis, and that light radiation of wavelengths more particularly of from 280 nm to 320 nm, i.e., UV-B irradiation, causes skin burning and erythema which can impair the development of a natural tan. For these reasons, as well as for aesthetic reasons, there is an increasing demand for means of controlling this natural tanning in order to thereby control the color of the skin. This UV-B radiation must thus be screened from the skin.

It is also known to this art that UV-A radiation, of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, for aesthetic and cosmetic reasons, such as conservation of the natural elasticity of the skin, for example, an ever-increasing number of individuals wish to control the effect of UV-A rays on their skin, it is desirable to also screen out UV-A radiation.

A wide variety of compounds suited for photoprotection (UV-A and/or UV-B) of the skin are known to this art. Most of these are aromatic compounds exhibiting absorption of UV radiation in the region from 280 to 315 nm, or in the region from 315 to 400 nm, or in both of these regions. There is no good way known at present to modify the absorption properties of molecules to meet the specific needs, or to combine products to cover a wide range of UV wavelengths. Products heretofore known are typically formulated into antisun or sunscreen compositions which are in the form of an emulsion of oil-in-water type (namely, a cosmetically acceptable vehicle, diluent or carrier comprising a dispersing continuous aqueous phase and a dispersed discontinuous oily phase) and which thus contain, in various concentrations, one or more conventional lipophilic and/or hydrophilic organic screening agents. These are capable of selectively absorbing harmful UV radiation of specific wavelength, depending upon structure of such screening agents (and their amounts) being selected as a function of the desired sun protection factor SPF (the sun protection factor being expressed mathematically by the ratio of the irradiation time required to attain the erythema-forming threshold with the UV screening agent to the time required to attain the erythema-forming threshold in the absence of UV screening agent).

It is a long felt need to have a sunscreening agent that can absorb ultra violet radiation at specific desired wavelengths and be soluble in water or oil. In addition, these compounds exhibiting anti-UV activity must also have good cosmetic properties in compositions comprised thereof, good solubility in the usual solvents, and in particular fatty substances such as oils and greases, as well as good resistance to water and to perspiration (remanence).

U.S. Pat. No. 6,080,880 issued Jun. 27, 2000 teaches that grafting at least one cinnamamide, benzalmalonamide or benzalmalonate group onto a short-chain silicone molecule, in particular onto a linear silicone chain comprising not more than six Si atoms, novel compounds are obtained which obviate the drawbacks of the screening agents of the prior art, these novel compounds having, other than very high-performance screening properties, very good solubility in the usual organic solvents and in particular fatty substances such as oils, as well as excellent cosmetic properties, which render them particularly suitable for use as sunscreens in, or for the formulation of, cosmetic compositions suited for protecting the skin and/or the hair against the deleterious effects of ultraviolet radiation. The teachings state "And, taking account of their relatively small size, these novel compounds are easier to synthesize".

After reviewing the teachings of U.S. Pat. No. 6,080,880 and specifically the findings that low molecular are desirable, we have surprisingly found that the making of specific compounds of the present invention, higher molecular weight compounds can be made that have the added attributes of being able to control the UV spectra, solubility in a variety of solvents and because of their molecular weight stay on the skin surface, rather than penetrate it as is the case with low molecular weight species.

3. Summary of the Invention

A major object of the present invention is the provision of novel silicone compounds that contain a UV-absorber and a polar alkoxylated group. The presence of the polar alkoxylated group not only has a dramatic effect upon solubility of the sunscreen, but also shifts the UV absorption properties, making it possible to synthesize products that have a specified UV absorption property. Since UV-B is the major area that causes problems with sun tanning, the products can be customized to have the desired water or oil solubility as well as the desired UV spectra. These novel compounds can be prepared to have the desired spectra, in addition to very good solubility in fatty materials, or aqueous systems, improved cosmetic properties, and which otherwise avoid those disadvantages and drawbacks to date characterizing the state of this art. This allows for the ability to formulate products heretofore unavailable to the cosmetic chemist.

Thus, the present invention features novel compounds having the formula

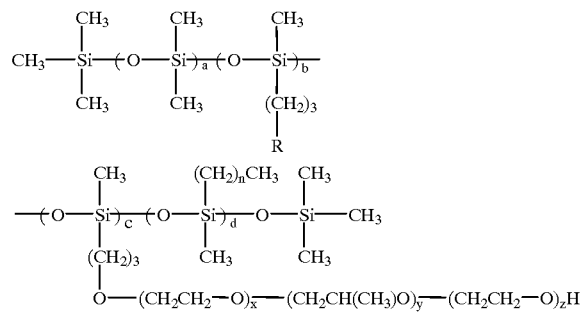

wherein;

R is 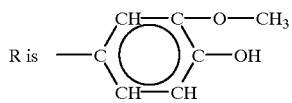

a is an integer ranging from 0 to 2000;
b is an integer ranging from 1 to 20;
c is an integer ranging from 1 to 20;
d is an integer ranging from 0 to 20;
n is an integer ranging from 10 to 20;
w is an integer ranging 0 to 20;
x is an integer ranging 0 to 20;
y is an integer ranging 0 to 20;
z is an integer ranging 0 20.

DETAILED DESCRIPTION OF THE INVENTION

Objective of the Invention

It is the objective of the present invention to provide a series of novel silicone compounds that contain a UV absorber, derived from eugenol, and a polar hydroxyl-containing group referred to herein as a dimethicone copolyol group. The dimethicone copolyol group functions not only to alter the UV absorption properties of the compounds making them acceptable UV-B screens, but also modifies the solubility of the silicone compounds making them acceptable for formulation into water, silicone and oil phases.

It is also the objective of the present invention to provide a process for protecting skin and hair from the negative effects of the sun by applying an effective amount of a compound of the present invention.

It is also the objective of the present invention to provide a process for protecting textile fibers fabrics and plastics from the negative effects of the sun by applying an effective amount of a compound of the present invention.

Other objectives will become clear from reading the specifications and claims of the present application.

Detailed Description of the Invention

The compounds of the present invention conform to the formula;

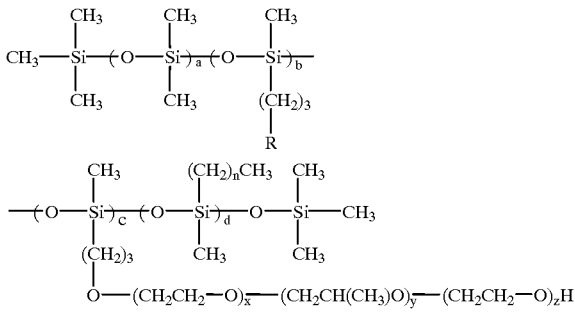

wherein;

R is 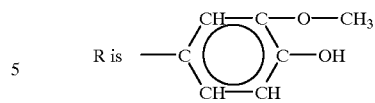

a is an integer ranging from 0 to 2000;
b is an integer ranging from 1 to 20;
c is an integer ranging from 1 to 20;
d is an integer ranging from 0 to 20;
n is an integer ranging from 10 to 20;
w is an integer ranging 0 to 20;
x is an integer ranging 0 to 20;
y is an integer ranging 0 to 20;
z is an integer ranging 0 to 20.

One of the inventive aspects of the present invention is not only the UV absorber of used as a raw material in the practice of the present invention is which is euganol, but also the surprising finding that when polar groups are incorporated, in this case dimethicone copolyol groups (the group covered by subscript "c") the UV absorption spectra shifts into the UV-B region. Or stated another way, when c is zero, the UV absorption is in the UV-C region. This wavelength of UV is of interest only in certain high-energy states like welding, or in high altitude applications like aerospace. Since the sunscreening wavelengths are UV-B the molecules wherein c is 0 are not effective. This incorporation of the "c" subunit also allows for the variation of solubility. If the value of "x" is high, the product will be water-soluble. If the value of "y" is high the product will be more soil soluble. If the value of a "a" is high the molecule will have increased solubility in silicone. If the "d" value is high the oil solubility and increases and the product will be a wax. In short, the proper selection of compounds within the scope of the present invention will allow for customized products that vary in physical form (liquid or solid), solubility (oil, water or silicone), water resistance (remanence) and UV absorbing properties. This offers the formulator latitude to make products heretofore unimaginable.

Preferred Embodiment

In a preferred embodiment d is 0.

In a preferred embodiment x and y are each 0.

In a preferred embodiment x is an integer ranging from 4 to 10.

In a preferred embodiment y is an integer ranging from 0 to 10.

In a preferred embodiment wherein x is 8.

In a preferred embodiment b is an integer ranging from 2 to 10.

In a preferred embodiment b is an integer ranging from 4 to 6.

In a preferred embodiment x is 10.

In a preferred embodiment a is an integer ranging from 5 to 15.

In a preferred embodiment a is an integer ranging from 5 to 10.

In a preferred embodiment a is 9.

In a preferred embodiment d ranges from 1 to 20.

EXAMPLES

Raw Materials

1. Polymer Synthesis

Preparation of Silanic Hydrogen Containing Intermediates

Silicone intermediates of the type used to make the compounds of this invention are well known to those skilled in the art. International Publication (Silicone Alkylene Oxide Copolymers As Foam Control Agents) WO 86/05411 by Paul Austin (Sep. 25, 1986) p16 (examples 1 to 6) teaches how to make the following intermediates, and is incorporated herein by reference.

Hydrosilylation

Silanic Hydrogen Containing Compounds (Comb Type)

The polymers used as raw materials are known to those skilled in the art and conform to the following structure:

$$CH_3-Si(CH_3)_2-(O-Si(CH_3)_2)_a-(O-Si(CH_3)(H))_b-O-Si(CH_3)_2-CH_3$$

Compounds of this type are available from Siltech Corporation Toronto Ontario Canada.

| Example | Austin Example | a | b | Average Molecular Weight | Equivalent Molecular |
|---|---|---|---|---|---|
| 1 | 1 | 20 | 3 | 1,850 | 551 |
| 2 | 4 | 160 | 5 | 24,158 | 4,831 |
| 3 | 6 | 20 | 10 | 2,258 | 225 |

Compounds of this type are also available commercially from Siltech Corporation Toronto Ontario Canada. The structures were determined using silicone nmr and the chemistries were described using experimentally determined structures. Trade names are given merely for reference.

| Example | Siltech Name | | a | b |
|---|---|---|---|---|
| 4 | Siltech | D-116 | 9 | 4 |
| 5 | Siltech | H-345 | 22 | 5 |
| 6 | Siltech | C-106 | 50 | 10 |
| 7 | Siltech | ZZ-302 | 70 | 20 |
| 8 | Siltech | XX-456 | 50 | 60 |
| 9 | Siltech | J-456 | 10 | 20 |
| 10 | Siltech | G-456 | 0 | 60 |

2. UV Absorber

Example 11

The UV absorber of used as a raw material in the practice of the present invention is eugenol. Eugenol is 2-methoxy-4-(2 propenyl)phenol. It has a molecular weight of 164.20 and is commercially available from many sources. It conforms to the following structure:

$$CH=CH-CH_2-C_6H_3(OCH_3)(OH)$$

As will become clear from the invention, eugenol by itself absorbs UV in the UV-C region making it unacceptable for sun screen applications. Only when made into a compound of the present invention does the aspectra shift into the UV-B region.

3. Alkoxylated Allyl Alcohols

Alkoxylated allyl alcohol conforms to the following structure:

$$CH_2=CH-CH_2-(CH_2CH_2-O)_x-(CH_2CHCH_3O)yH$$

wherein x and y are integers independently ranging from 0 to 20.

Compounds of this type are also available commercially from Siltech Corporation Toronto Ontario Canada. The structures were determine using carbon nmr and wet analysis. The chemistries were described using experimentally determined structures. Trade names are given merely for reference.

| Example | x | y |
|---|---|---|
| 12 | 0 | 0 |
| 13 | 8 | 0 |
| 14 | 20 | 20 |
| 15 | 16 | 8 |
| 16 | 5 | 5 |
| 17 | 25 | 25 |
| 18 | 12 | 6 |
| 19 | 9 | 9 |
| 20 | 0 | 9 |

4. Alpha Olefin

Alpha olefins are items of commerce and are available from a variety of sources including Chevron. They conform to the following structure:

$$CH_2=CH-(CH_2)_sCH_3$$

s is an integer ranging from 8 to 18 and is equal to n-2.

| Example | s |
|---|---|
| 21 | 8 |
| 22 | 10 |
| 23 | 12 |
| 24 | 14 |
| 25 | 18 |

5. Hydrosilylation

The hydrosilylation reaction used to make the compounds of this invention is well known to those skilled in the art. One of many references is International Publication (Silicone Alkylene Oxide Copolymers As Foam Control Agents) WO 86/05411 by Paul Austin (Sep. 25, 1986) p. 19. General Reaction Process (Hydrosilylation)

To a suitable flask fitted with a mechanical agitator, thermometer with a Therm-o-watch temperature regulator, nitrogen sparge tube vented reflux condenser and heating mantle is added the specified quantity of eugenol (example 11), allyl alcohol alkoxylates (examples 12–20), and alpha olefin (examples 21–25) examples. Next is added the specified number of grams of the specified hydrosilylation intermediate (Example # 1–10) and isopropanol. The temperature is increased to 85° C. and 3.5 ml of 3% $H_2PtCl_6$ in ethanol is added. An exotherm is noted to about 95° C., while the contents are stirred for about 2 hours. During this time silanic hydrogen concentration drops to nil. Cool to 65° C. and slowly add 60 g of sodium bicarbonate. allow to mix overnight and filter through a 4-micron pad. Distill off any solvent at 100° C. and 1 torr.

Example 26

To a suitable flask fitted with a mechanical agitator, thermometer with a Therm-o-watch temperature regulator, nitrogen sparge tube vented reflux condenser and heating mantle is added 396.9 grams of eugenol (example 11), 915.4 grams of allyl alcohol alkoxylate (example 16), 1687.7 grams of hydrosilylation intermediate (Example # 15) and 750 grams of isopropanol.

Heat to 85° C. and add 3.5 ml of 3% $H_2PtCl_6$ in ethanol. An exotherm is noted to about 95° C., while the contents are stirred for about 2 hours. During this time silanic hydrogen concentration drops to nil. Cool to 65° C. and slowly add 60 g of sodium bicarbonate, allow to mix overnight and filter through a 4-micron pad. Distill off any solvent at 100° C. and 1 torr.

Example

|         | Silanic Polymer |        | Euganol |        | Allyl Alkoxylate |        | Alpha Olefin |        |
|---------|---------|--------|---------|--------|---------|--------|---------|--------|
| Example | Example | Grams  | Example | Grams  | Example | Grams  | Example | Grams  |
| 23 | 1  | 2600.8 | 11 | 233.9 | 12 | 165.2  | 21 | 0     |
| 24 | 2  | 2617.0 | 11 | 34.9  | 13 | 348.1  | 21 | 0     |
| 25 | 3  | 497.1  | 11 | 181.7 | 14 | 2321.2 | 21 | 0     |
| 26 | 4  | 703.4  | 11 | 107.9 | 15 | 2188.6 | 21 | 0     |
| 27 | 5  | 1522.5 | 11 | 238.7 | 16 | 1238.7 | 21 | 0     |
| 28 | 6  | 522.7  | 11 | 38.4  | 17 | 2438.9 | 21 | 0     |
| 29 | 7  | 423.0  | 11 | 53.0  | 18 | 2524.0 | 21 | 0     |
| 30 | 8  | 387.3  | 11 | 85.1  | 19 | 2527.6 | 21 | 0     |
| 31 | 9  | 543.5  | 11 | 211.8 | 20 | 2244.7 | 21 | 0     |
| 32 | 10 | 1360.6 | 11 | 592.0 | 12 | 1046.6 | 21 | 0     |
| 33 | 1  | 2064.2 | 11 | 185.6 | 13 | 463.5  | 21 | 286.6 |
| 34 | 2  | 1942.5 | 11 | 25.9  | 14 | 991.7  | 22 | 39.9  |
| 35 | 3  | 691.9  | 11 | 101.1 | 15 | 2050.9 | 23 | 156.1 |
| 36 | 4  | 1223.6 | 11 | 187.7 | 16 | 1298.7 | 24 | 289.8 |
| 37 | 5  | 607.9  | 11 | 47.7  | 17 | 2270.9 | 25 | 73.6  |
| 38 | 6  | 1229.4 | 11 | 90.3  | 18 | 1540.8 | 21 | 139.4 |
| 39 | 7  | 886.1  | 11 | 66.6  | 19 | 1978.8 | 22 | 68.5  |
| 40 | 8  | 581.7  | 11 | 63.9  | 20 | 2255.8 | 23 | 98.6  |
| 41 | 9  | 1589.3 | 11 | 371.7 | 12 | 656.4  | 24 | 382.5 |
| 42 | 10 | 429.1  | 11 | 93.4  | 13 | 2333.2 | 25 | 144.3 |

|         | Silanic Polymer |        | Euganol |        | Allyl Alkoxylate |        | Alpha Olefin |        |
|---------|---------|--------|---------|--------|---------|--------|---------|--------|
| Example | Example | Grams  | Example | Grams  | Example | Grams  | Example | Grams  |
| 43 | 1  | 1261.7 | 11 | 113.5 | 15 | 1449.7 | 21 | 175.2 |
| 44 | 2  | 2430.1 | 11 | 32.4  | 15 | 437.6  | 22 | 99.9  |
| 45 | 3  | 1038.5 | 11 | 151.8 | 16 | 1575.3 | 23 | 234.4 |
| 46 | 4  | 478.9  | 11 | 73.5  | 17 | 2334.1 | 24 | 113.4 |
| 47 | 5  | 1182.4 | 11 | 92.7  | 18 | 1581.8 | 25 | 143.1 |
| 48 | 6  | 1201.7 | 11 | 88.3  | 19 | 1573.8 | 21 | 136.3 |
| 49 | 7  | 1209.9 | 11 | 90.9  | 20 | 1605.6 | 22 | 93.6  |
| 50 | 8  | 1799.5 | 11 | 197.6 | 12 | 697.9  | 23 | 305.0 |
| 51 | 9  | 665.1  | 11 | 103.7 | 13 | 2071.2 | 24 | 160.1 |
| 52 | 10 | 123.1  | 11 | 53.6  | 14 | 2740.5 | 25 | 82.8  |
| 53 | 4  | 1,066  | 11 | 164   | 13 | 1,228  | 21 | 0     |
| 54 | 4  | 534    | 11 | 164   | 13 | 409    | 21 | 0     |
| 55 | 4  | 355    | 11 | 164   | 13 | 136    | 21 | 0     |

Comparison Compound (no allyl alkoxylate group)

| | Silanic Polymer | | Euganol | | Allyl Alkoxylate | | Alpha Olefin | |
|---|---|---|---|---|---|---|---|---|
| Example | Example | Grams | Example | Grams | Example | Grams | Example | Grams |
| 56 | 4 | 267 | 11 | 164 | 13 | 0 | 21 | 0 |

Applications Examples

The effectiveness of the technology of the current invention can be demonstrated by the comparison of a very simple system. The following comparison is a common silicone backbone, with differing "b", and "c" values. The effect upon solubility at 5% in water and the UV maxima for the absorption are quite dramatic.

| Example | a | b | c | d | x | y | z | UV Absorbtion | Water Solubility |
|---|---|---|---|---|---|---|---|---|---|
| 53 | 9 | 1 | 3 | 0 | 8 | 0 | 0 | 325 nm (UV-B) | Soluble |
| 54 | 9 | 2 | 2 | 0 | 8 | 0 | 0 | 320 nm (UV-B) | Dispersible |
| 55 | 9 | 3 | 1 | 0 | 8 | 0 | 0 | 312 nm (UV-B) | Dispersible |

Comparison Compound

| Example | a | b | c | d | x | y | z | UV Absorbtion | Water Solubility |
|---|---|---|---|---|---|---|---|---|---|
| 56 | 9 | 4 | 0 | 0 | 8 | 0 | 0 | 280 nm (UV-C) | Insoluble |

It is most interesting and significant that the compound of example 56 has no dimethicone copolyol groups present in the molecule, but has the eugenol based UV absorber. The absorption is at 280 nm, which is the UV-C spectrum. This wavelength is too low to be of interest in sun protection. UV-C is filtered out by the atmosphere and is of concern only at levels above 20,000 feet and in certain high-energy situations like welding. The result is that the compound covered by example 56 is not a sunscreen. The making of compounds of the present invention, that is incorporation of polar dimethicone copolyol groups into the molecule results in a shifting of the spectra into the UV-B region (290–320 nm).

The compounds of the present invention as demonstrated in the above simple system allows one to tailor the compound to cover a wide range of wavelengths, or by blending cover a broad spectrum of wavelengths. The incorporation of FDA approved sunscreen agents into emulsions that contain the compounds of the present invention are used as auxiliaries and or emulsifiers is expected to give the optimum performance.

In addition the compounds of the present invention can be placed on textile fabrics, commonly canvas as used in commercial awnings. The compounds would not only render the canvas soft, but also provide protection over a wide range of UV conditions.

Another application is to use the compounds of the present invention to soften garments. This would not only protect the garment from UV degradation, but also provide the wearer of the shirt a level of sun protection.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A silicone polymer conforming to the following structure:

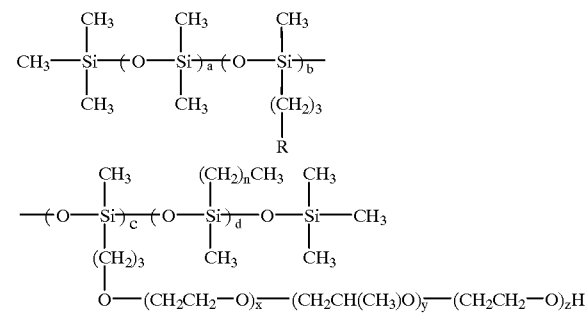

wherein;

R is 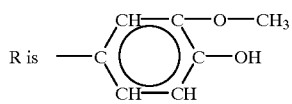

a is an integer ranging from 0 to 2000;
b is an integer ranging from 1 to 20;
c is an integer ranging from 1 to 20;
d is an integer ranging from 1 to 20;
n is an integer ranging from 10 to 20;
x is an integer ranging 0 to 20;

y is an integer ranging 0 to 20;

z is an integer ranging 0 to 20.

2. A silicone polymer of claim 1 wherein n is 15.

3. A silicone polymer of claim 1 wherein n is 17.

4. A silicone polymer of claim 1 wherein n is 11.

5. A silicone polymer of claim 1 wherein b is an integer ranging from 5 to 10.

6. A silicone polymer of claim 1 wherein b is 4.

7. A silicone polymer of claim 1 wherein n is 13.

8. A silicone polymer of claim 1 wherein a is 9.

9. A silicone polymer of claim 1 wherein x and y are each 0.

10. A silicone polymer of claim 1 wherein x is an integer ranging from 4 to 10.

11. A silicone polymer of claim 1 wherein y is an integer ranging from 0 to 10.

12. A silicone polymer of claim 1 wherein x is 8.

13. A silicone polymer of claim 1 wherein b is an integer ranging from 2 to 10.

14. A silicone polymer of claim 1 wherein b is an integer ranging from 4 to 6.

15. A silicone polymer of claim 1 wherein x is 10.

16. A silicone polymer of claim 1 wherein a is an integer ranging from 5 to 15.

17. A silicone polymer of claim 1 wherein a is an integer ranging from 5 to 10.

* * * * *